(12) United States Patent
Couture et al.

(10) Patent No.: US 10,878,965 B2
(45) Date of Patent: Dec. 29, 2020

(54) PATIENT-SPECIFIC CUTTING BLOCK AND METHOD OF MANUFACTURING SAME

(71) Applicant: ZIMMER, INC., Warsaw, IN (US)

(72) Inventors: Pierre Couture, Montreal (CA);
Vincent Masse, Montreal (CA);
Anselm Jakob Neurohr, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 38 days.

(21) Appl. No.: 16/248,051

(22) Filed: Jan. 15, 2019

(65) Prior Publication Data

US 2019/0148022 A1 May 16, 2019

Related U.S. Application Data

(62) Division of application No. 14/729,505, filed on Jun. 3, 2015, now Pat. No. 10,217,530.

(60) Provisional application No. 62/007,124, filed on Jun. 3, 2014.

(51) Int. Cl.
*A61B 34/10* (2016.01)
*G16H 50/50* (2018.01)
*G06F 19/00* (2018.01)

(52) U.S. Cl.
CPC ............ *G16H 50/50* (2018.01); *A61B 34/10* (2016.02); *G06F 19/00* (2013.01); *A61B 2034/102* (2016.02)

(58) Field of Classification Search
CPC ......... G16H 50/50; A61B 34/10; G06F 19/00; G06F 19/3437; G06F 2034/102

USPC .......... 606/87–89, 79, 82, 96, 86 R; 700/98; 703/1

See application file for complete search history.

(56) References Cited

U.S. PATENT DOCUMENTS 4,841,975 A  6/1989  Woolson
5,098,383 A  3/1992  Hemmy et al.
(Continued)

FOREIGN PATENT DOCUMENTS

AU  2004293091 A1  6/2005
AU  2004293104 A1  6/2005
(Continued)

OTHER PUBLICATIONS

Hofmann et al, "Natural-Knee II System", Intermedics Orthopedics, Austin, TX, 1995.

*Primary Examiner* — Pedro Philogene
(74) *Attorney, Agent, or Firm* — Norton Rose Fulbright Canada LLP

(57) ABSTRACT

A patient-specific cutting assembly comprises a model file including geometrical data of a bone of the patient, of an intramedullary canal of the bone, and a planned orientation of a cutting block. A fixing rod is adapted to be longitudinally inserted and extending partially from the intramedullary canal. A patient-specific cutting block is connectable to the fixing rod. The patient-specific cutting block includes a structure having a patient specific geometry corresponding to the model file of the patient, the structure configured to be connected to a portion of the fixing rod projecting from the bone in a unique coupling orientation. A cutting guide is connected to the structure, the cutting guide being in the planned orientation when the structure is connected to the portion of the fixing rod projecting from the bone.

8 Claims, 7 Drawing Sheets

(56) References Cited

U.S. PATENT DOCUMENTS

| | | | |
|---|---|---|---|
| 5,179,915 A * | 1/1993 | Cohen | A61B 17/1717 606/62 |
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 5,928,240 A * | 7/1999 | Johnson | A61B 17/885 606/79 |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz | |
| 2004/0236424 A1 | 11/2004 | Berez et al. | |
| 2005/0203524 A1 | 9/2005 | Penenberg | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0087276 A1 | 4/2009 | Rose | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |
| 2010/0082035 A1 | 4/2010 | Keefer | |
| 2010/0087829 A1 | 4/2010 | Metzger et al. | |
| 2010/0152741 A1 | 6/2010 | Park et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0174376 A1 | 7/2010 | Lang et al. | |
| 2010/0185202 A1 | 7/2010 | Lester et al. | |
| 2010/0191244 A1 | 7/2010 | White et al. | |
| 2010/0211077 A1 * | 8/2010 | Couture | A61B 34/20 606/88 |
| 2010/0212138 A1 | 8/2010 | Carroll et al. | |
| 2010/0217270 A1 | 8/2010 | Polinski et al. | |
| 2010/0217338 A1 | 8/2010 | Carroll et al. | |
| 2010/0228257 A1 | 9/2010 | Bonutti | |
| 2010/0234849 A1 | 9/2010 | Bouadi | |
| 2010/0256479 A1 | 10/2010 | Park et al. | |
| 2010/0262150 A1 | 10/2010 | Lian | |

(56) References Cited

U.S. PATENT DOCUMENTS

| | | |
|---|---|---|
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0130761 A1 | 6/2011 | Plaskos et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0275957 A1 | 11/2011 | Bhandari |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz |
| 2012/0245699 A1 | 9/2012 | Lang et al. |
| 2012/0259420 A1 | 10/2012 | Lashure et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2012/0296339 A1 | 11/2012 | Iannotti et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0131681 A1* | 5/2013 | Katrana .............. A61B 17/846 606/87 |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |

(56) References Cited

U.S. PATENT DOCUMENTS

| | | | |
|---|---|---|---|
| 2014/0074441 A1 | 3/2014 | Fitz et al. | |
| 2014/0086780 A1 | 3/2014 | Miller et al. | |
| 2014/0257309 A1* | 9/2014 | Aram | A61B 17/1721 606/88 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 101878002 A | 11/2010 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |

(56) References Cited

FOREIGN PATENT DOCUMENTS

| | | | |
|---|---|---|---|
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013/136302 A1 | 9/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

\* cited by examiner

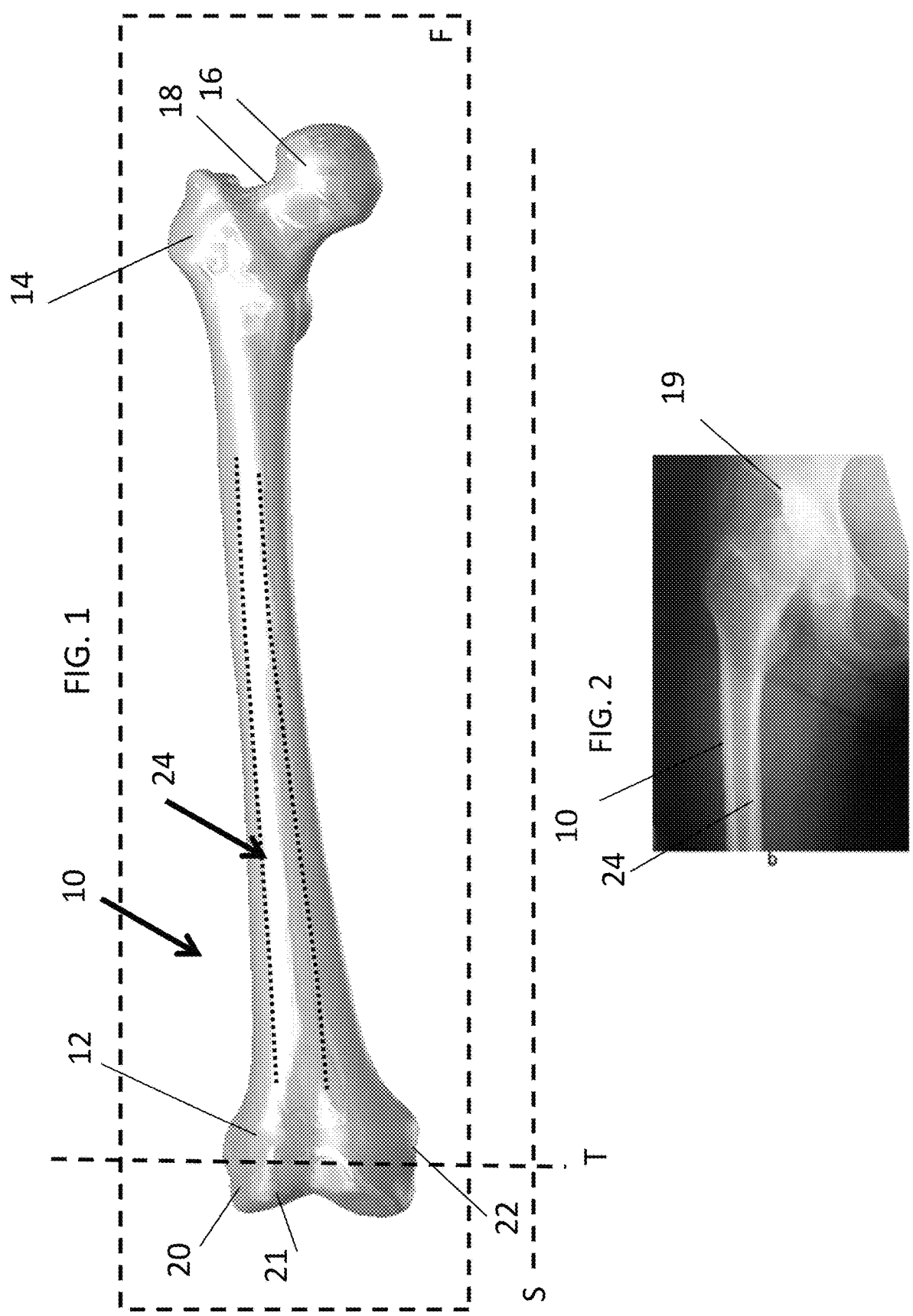

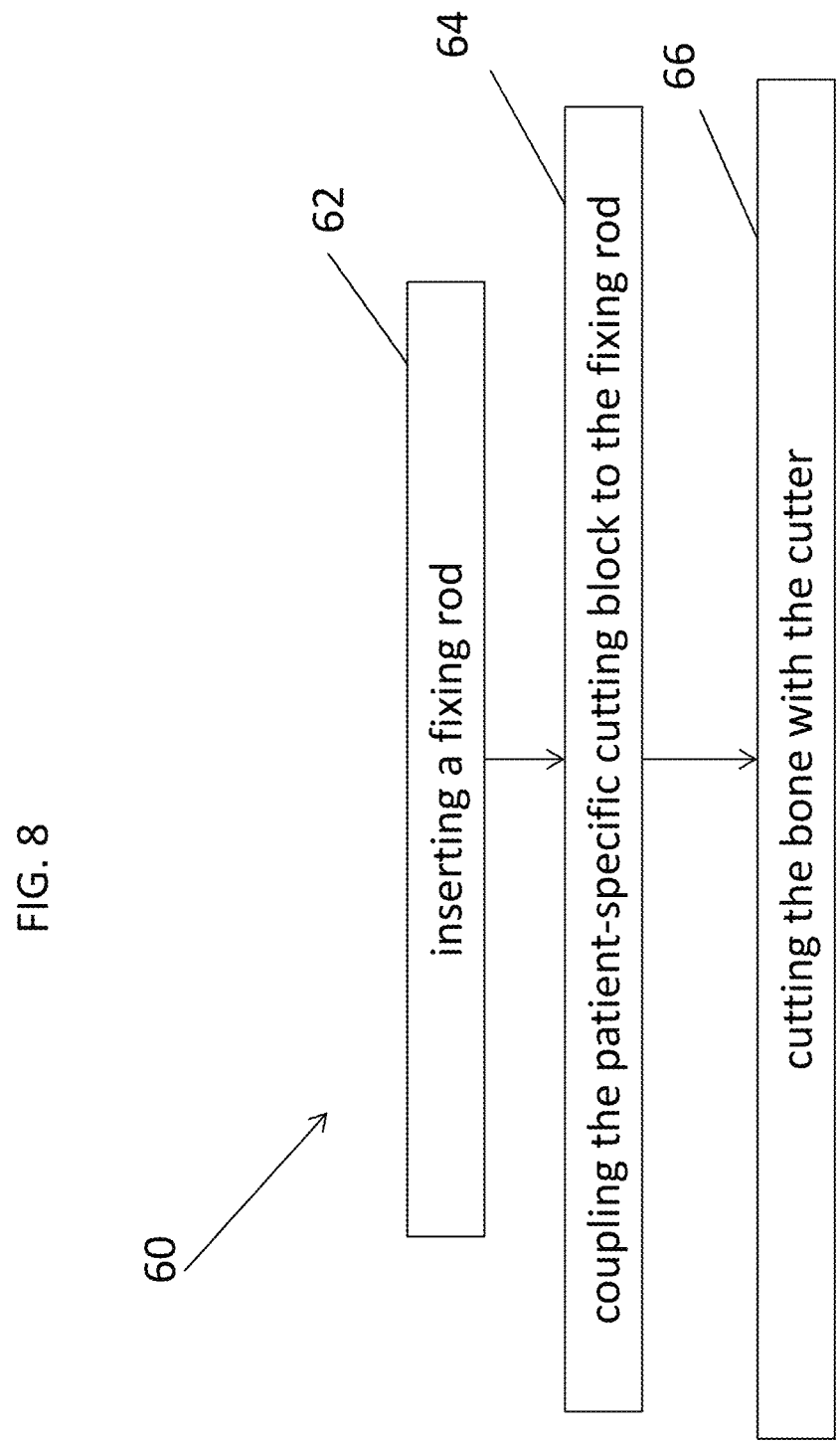

PATIENT-SPECIFIC CUTTING BLOCK AND METHOD OF MANUFACTURING SAME

CROSS-REFERENCE TO RELATED APPLICATION

The present application is a divisional application of Ser. No. 14/729,505 filed on Jun. 3, 2015, which claims priority on U.S. Provisional Patent Application No. 62/007,124, filed on Jun. 3, 2014, and incorporated herein by reference.

TECHNICAL FIELD

The application relates generally to orthopedic surgery involving the preparation of bones with a view to fixing an implant thereon and, more particularly, to devices and tools developed in planning for assisting orthopedic surgery.

BACKGROUND

Before posing an implant onto a bone, such as during a knee or hip replacement surgery, the bone needs to be prepared. The preparation of the bone includes removing diseased bone, for example, and making additional cuts so that the bone has a shape matching that of an inside of the implant, or drilling holes, placing guides, etc for providing guidance landmarks to an operator. For instance, in knee implant surgery, transverse and frontal cut planes are made to match surfaces of an implant.

Determination of alterations to the bone, of the portions of the bone that need to be removed, of guides to be placed may be done prior to surgery using images of the bone of the patient, in pre-operative planning. The pre-operative planning may help in ensuring the precision and accuracy of the surgery, as bone alterations will influence the fit of the implant onto the bone. For example, a bone that has been improperly cut may lead to improper implant placement, resulting in conditions such as leg length discrepancy, improper gait, premature implant wear, and pain, to name a few.

SUMMARY

Therefore, in accordance with a first embodiment of the present disclosure, there is provided a method of creating a model of a patient-specific structure of a cutting block, the cutting block used for assisting an operator in cutting at least one plane in a bone of a patient, the method comprising: obtaining geometrical data of a bone and of an intramedullary canal of the bone; determining a penetration of a fixing rod to be inserted in and extending partially out from an intramedullary canal of the bone, the penetration based on the geometrical data of the intramedullary canal of the bone and on a geometry of the fixing rod; determining an orientation of a portion of the fixing rod projecting out of the bone relative to the bone based on the geometrical data of the bone, on the geometry of the fixing rod and on the penetration; and creating the model of the patient-specific structure of the cutting block using the geometrical data of the bone, a desired position and orientation of the at least one cut plane on the bone, and the orientation of the portion of the fixing rod projecting out of the bone.

Further in accordance with the first embodiment, creating the model comprises determining an orientation of a bore to be formed through the patient-specific structure, the bore being adapted to connect to the portion of the fixing rod in a unique coupling orientation.

Still further in accordance with the first embodiment, determining the orientation of the portion of the fixing rod projecting out of the bone relative to the bone comprises determining an orientation of the portion relative to a bone axis as the geometrical data of the bone.

Still further in accordance with the first embodiment, obtaining geometrical data of a bone comprises obtaining a mechanical axis of the bone.

Still further in accordance with the first embodiment, determining the orientation of the portion relative to the bone axis comprises obtaining a spatial angle between an axis of the portion of the fixing rod and the bone axis.

Still further in accordance with the first embodiment, instructions are created based on the model of the patient-specific structure for manufacturing the patient-specific structure.

Still further in accordance with the first embodiment, the patient-specific structure is manufactured based on the instructions.

Still further in accordance with the first embodiment, the desired position and orientation of the cutting plane of the bone is determined using a model of an implant.

Still further in accordance with the first embodiment, creating the model comprises modelling patient-specifically an attachment of the cutting guide to the patient-specific structure based on an orientation of the patient-specific structure relative to the bone and of geometrical data of the bone.

Still further in accordance with the first embodiment, instructions are created based on the patient-specific attachment model for manufacturing the patient-specific cutting attachment.

Still further in accordance with the first embodiment, the patient-specific cutting attachment is manufactured based on the instructions.

In accordance with a second embodiment of the present disclosure, there is provided a patient-specific cutting assembly, the assembly comprising: a model file including geometrical data of a bone of the patient, of an intramedullary canal of the bone, and a planned orientation of a cutting block; a fixing rod adapted to be longitudinally inserted in and extending partially from the intramedullary canal; and a patient-specific cutting block connectable to the fixing rod, the patient-specific cutting block including at least: a structure having a patient specific geometry corresponding to the model file of the patient, the structure configured to be connected to a portion of the fixing rod projecting from the bone in a unique coupling orientation; and a cutting guide connected to the structure, the cutting guide being in the planned orientation when the structure is connected to the portion of the fixing rod projecting from the bone.

Further in accordance with the second embodiment, the structure has a bore extending through opposed first and second faces thereof, the bore having a diameter allowing the fixing rod to be inserted thereinto, the bore being formed in the structure at an orientation based on the model file.

Still further in accordance with the second embodiment, an orientation of the bore in the structure is based on a predetermined bone axis.

Still further in accordance with the second embodiment, the predetermined bone axis is a mechanical axis of the bone.

Still further in accordance with the second embodiment, a face of the structure is adapted to abut the bone, the face of the structure has a shaped that is a negative of a surface of the bone obtained as the geometrical data of the bone of the patient.

Still further in accordance with the second embodiment, the fixing rod has a geometry that is a negative of an inner surface of the intramedullary canal obtained as the geometrical data of the intramedullary canal.

In accordance with a third embodiment of the present disclosure, there is provided a method of cutting a bone of a patient in preparation of placement of an implant onto the bone, the method comprising: inserting a fixing rod longitudinally in an intramedullary canal of the bone with a portion of the fixing rod extending outside the bone; connecting a patient-specific structure of a cutting block onto the portion of the fixing rod extending outside the bone and placing a cutting guide of the patient-specific cutting block in abutment with the bone in a unique coupling orientation; and cutting the bone with the cutting guide.

Further in accordance with the third embodiment, connecting the patient-specific structure comprises anchoring the patient-specific structure to the bone and removing the fixing rod.

In another aspect, there is provided a method of manufacturing a patient-specific structure of a cutting block, the structure providing a support to a cutting guide for cutting a plane in a bone of a patient, the method comprising: predicting an orientation of a fixing rod to be inserted in and extending partially from an intramedullary canal of the bone, the prediction of the orientation of the fixing rod being based on a known orientation of the intramedullary canal of the bone; determining an orientation of the fixing rod relative to a bone axis, the bone axis being determined using data of the bone, the determination of the orientation of the fixing rod being achieved by modelling the fixing rod inserted in the intramedullary canal; and modelling the patient-specific structure of the cutting block for manufacture thereof, the modelling including modelling a bore to be formed through the patient-specific structure, the bore being adapted to connect to the fixing rod, the bore having an orientation relative to the patient-specific structure dependent on the orientation of the fixing rod relative to the bone axis.

In yet another aspect, there is provided a patient-specific cutting assembly, the assembly comprising: a fixing rod adapted to be longitudinally inserted in and extending partially from an intramedullary canal of a bone of a patient; and a patient-specific cutting block connectable to the fixing rod, the patient-specific cutting block including: a structure comprising: opposed first and second faces; and a bore extending through opposed first and second faces, the bore having a diameter allowing the fixing rod to be inserted thereinto, the bore being formed in the structure at an orientation based on an orientation of the fixing rod should have when inserted in the intramedullary canal and on an orientation of a predetermined bone axis, the predetermined bone axis being determined using data of the bone, the structure when inserted into the fixing rod having a fixed orientation; and a cutting guide connected to the structure, the cutting guide being parallel to the opposed first and second faces, the cutting guide being at a distance from the structure based on an implant selected for the bone of the patient.

In yet another aspect, there is provided a method of cutting a bone of a patient in preparation of placement of an implant onto the bone, the method comprising: inserting a fixing rod longitudinally in an intramedullary canal of the bone with a portion of the fixing rod extending outside the bone; inserting a patient-specific structure of a cutting block onto the portion of the fixing rod extending outside the bone and placing a cutting guide of the patient-specific cutting block in abutment with the bone, the structure having opposed first and second faces and a bore therethrough, an orientation of the bore relative to the structure being predetermined as a function of an orientation of the fixing rod relative to the intramedullary canal and of a bone axis, the bone axis being predetermined using data of the bone, the bore providing a fixed patient-specific orientation of the structure relative to the bone, the cutting guide extending from the first face at a predetermined distance, the predetermined distance being dependent on the implant selected for the bone; and cutting the bone with the cutting guide.

DESCRIPTION OF THE DRAWINGS

Reference is now made to the accompanying figures in which:

FIG. 1 is a schematic view of a human femur;

FIG. 2 is an X-ray image of a femur;

FIG. 8 is a flow chart of a method of cutting the femur of FIG. 1 with the patient-specific cutting block of FIG. 3.

DETAILED DESCRIPTION

Figure 3:
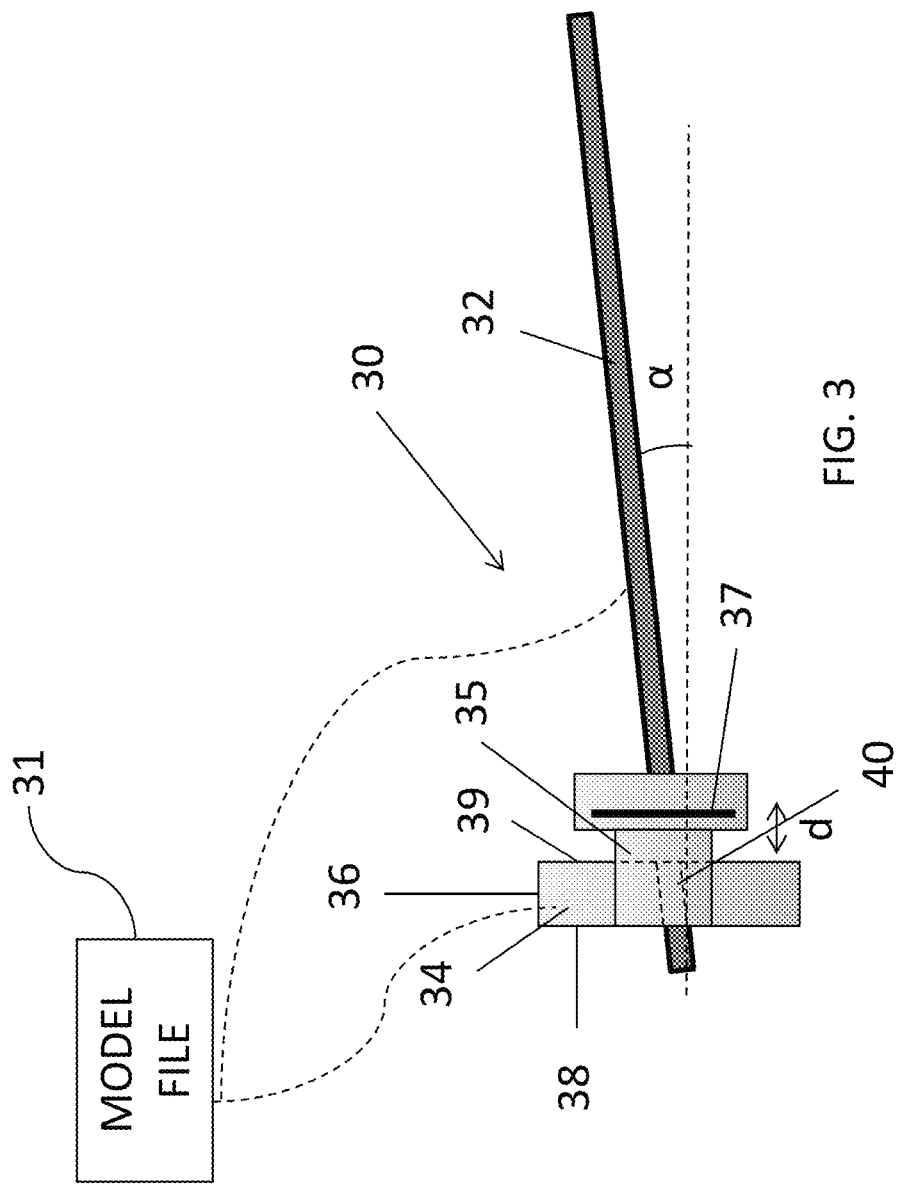
FIG. 3 is a schematic view of a patient-specific cutting block for the femur of FIG. 1.

The present disclosure will be made with reference to a human femur and a knee joint replacement surgery. It should be however understood that the disclosed devices and methods could be applied to human or animal bones other than the femur, to bone models, and implant surgeries other than knee joint replacement surgeries. Example of such bones include tibia, humerus and ulna, among others. The femur discussed herein being a 3-D component, spatial references will be made to "orientations". By orientation, it should be understood spatial orientation defined by the three Euler angles ($\theta$, $\varphi$, $\psi$) relative to a fixed frame of the bone. Also, references within this specification will be made to frontal plane (a.k.a. coronal plane), transverse plane (a.k.a. horizontal/vertical plane), and sagittal plane as commonly used as medical terminology.

With reference to FIG. 1, a human femur 10 is schematically shown along a frontal plane F. The femur 10 is the thigh bone and the longest bone in the body. A lower end 12 joins the tibia (not shown) to form the knee joint, while an upper end 14 is rounded into a femoral head 16 that fits into the acetabulum of the pelvis 19 (shown in FIG. 2) to form the hip joint. Just below the femoral head 16 is the femoral neck 18. The lower end 12 includes a lateral condyle 20 and a medial condyle 22, with a midpoint midway between the lateral condyle 20 and the medial condyle 22.

The femur 10, as other bones in the human body, is made of hard material, known as cortical bone, compact bone, forming the cortex of the bone. An inside of the bone contains a softer material called bone marrow. The bone marrow is contained in a portion called intramedullary canal 24 (shown in phantom in FIG. 1). The intramedullary canal 24 is non visible from the outside of the bone but can be seen on various medical imaging techniques such as X-rays used for example with magnetic resonance imagery to perform a 3-D reconstruction of the bone. The bone marrow being made of a material different from that of a rest of the bone, it may be contrasted out on the images. FIG. 2 shows an example of such imaging which enable to detect and define the intramedullary canal 24 in the bone, the bone portions being in a lighter shade of gray than the bone marrow. Hence, the geometry of the intramedullary canal 24 may be evaluated from the images, such as the X-rays.

The femur 10 is to be prepared in view of a knee joint replacement surgery by altering its knee-joint extremity in order to receive an implant (not shown) thereon. The lower end 12 is to be partially resurfaced to match a geometry of the implant for the implant to abut against the resurfaced knee joint in a predetermined position. The device and methods described herein allow tools such as a cutting block (a.k.a., positioning block, cut block, universal positioning block or tool) to be fabricated in part or as a whole as patient specific. The cutting block and other instruments described herein are said to be patient-specific, in that their geometries are modeled based on a planning for every patient's unique anatomy, using imaging techniques. Stated differently, the instruments such as the cutting block described hereinafter are developed subsequent to pre-operative steps by which a patient's anatomy is modeled and the implant position is defined. Hence, the instruments such as the cutting block described hereinafter have an identity related to a patient, and are most likely inadequate for being used with other patients, whereby the instruments are typically a one-time use instrument. Accordingly, the patient-specific instruments each have a model file of non-transient format which features a two-dimensional or three-dimensional model of the patient's anatomy resulting from pre-operative imaging. The specific geometry of the components of the patient-specific instruments are directly related to the contents of the model file. This means practically that data of the actual bone to be altered is used to manufacture portions or an entirety of the cutting block which once positioned relative to the femur 10, will be at a fixed predetermined and planned orientation and will guide a patient-specific cut of the femur 10.

Turning now to FIGS. 3 to 6, a patient-specific cutting assembly 30 includes a model file 31, a fixing rod 32 insertable in the intramedullary canal 24 of the femur 10, and a patient-specific cutting block 34 for cutting off portions of the bone, in preparation for implanting. The fixing rod 32 connects the patient-specific cutting block 34 to the femur 10.

The fixing rod 32 is a rigid rod selected to be inserted inside the intramedullary canal 24 of the femur 10. To that end, the fixing rod 32 is made of a biocompatible material. Examples of biocompatible materials include medical grade aluminum and medical grade titanium alloys. In order to be inserted inside the intramedullary canal 24, the fixing rod 32 is chosen to have a diameter smaller than that of the intramedullary canal 24 and to have a length allowing a portion to extend outside the femur 10. The diameter of the fixing rod 32 may not be chosen too small that the fixing rod 32 may radially displace in the intramedullary canal 24. At the same time, the diameter of the fixing rod 32 may not be chosen too large that the fixing rod 32 may alter the femur 10. Similarly, the length of the fixing rod 32 may not be chosen too short that the fixing rod 32 may not be secured in the intramedullary canal 24 and the cutting block 34 moves. The fixing rod 32, once inserted, should have a portion 32a extending from the femur 10 in order to attach a structure 36 of the cutting block 34 thereonto. The fixing rod 32 may be selected from a pool of already available rods or may be custom made to have a patient-specific geometry corresponding to that of the intramedullary canal 24. Hence, the fixing rod 32 may be one of the patient-specific instruments resulting from the pre-operative planning. In order to select the fixing rod 32, data on the femur 10 is analysed to determine a shape and size of the intramedullary canal 24. In one example, X-rays, such as the one of FIG. 2, are used to delimitate walls of the intramedullary canal 24, from which can be deduced a diameter and a length of the intramedullary canal 24. For instance, frontal and transverse X-rays may suffice in evaluating the geometry of the intramedullary canal 24 and predict a fit of the fixing rod 32 therein. In another example, a 3-D model of the intramedullary canal is created, and may be part of the model file 31, this embodiment being particularly useful when the fixing rod 32 has a geometry specific to the patient and thus shaped for custom and unique penetration in the intramedullary canal 24.

The patient-specific cutting block 34 includes the structure 36 to which one or more cutting guides 37 may be connected. Each of the cutting guide 37 has a cut slot, in which a blade may be inserted to guide in cutting the femur 10 along a plane of the cut slot. Other accessories may also be connected to the structure 36, such as drill guides, mill guides, reamer guides, in similar fashion to the cutting guide 37. The cutting guide 37 is removably connected to the structure 36 by an attachment 35. The cutting guide 37 and/or the attachment 35 may be selected from a pool of already made components or be patient-specific (i.e. manufactured based on patient's data), as a monolithic component with or without the structure 36. The attachment 35 may be connected to different locations on the structure 36 so as to orient cutting guide 37 and other alteration accessories to cut through different planes, such as the planes described above, or alter the bone at selected locations. In yet another embodiment, the cutting guide 37 are cut slots defined directly in the structure 36. According to another embodiment, temporary anchor holes are provided in the structure 36 to secure same to the femur F, after it has been positioned and oriented as planned relative to the femur F. This may allow the removal of the fixing rod 32, as the rod 32 could otherwise be in the way of cut blades. For example, lateral walls may project from the structure 36 for securing the structure 36 to medial/lateral portions of the femur F, which medial/lateral portions are not resurfaced during knee joint surgery.

In one non-limiting embodiment, the structure 36 has opposed first and second faces 38, 39. The second face 39 may abut the bone when installed onto the fixing rod 32. In order to provide a unique coupling orientation, the second face 39 may have a patient specific surface, being a negative of the bone it will abut, for unique complementary contact. Alternatively, the structure 36 may have abutments positioned as a function of the planning, again to ensure the unique coupling orientation. The structure 36 may made of a biocompatible material which may be same or different than the one used for the fixing rod 32. The structure 36 may have dimensions similar to that of the lower end 12 of the femur 10 against which it will abut (shown in FIG. 5). The structure 36 may be selected from a pool of already available structures or may be custom made based on preoperative data, such as model file 31, representative of the femur 10 it will be put onto.

Figure 4:
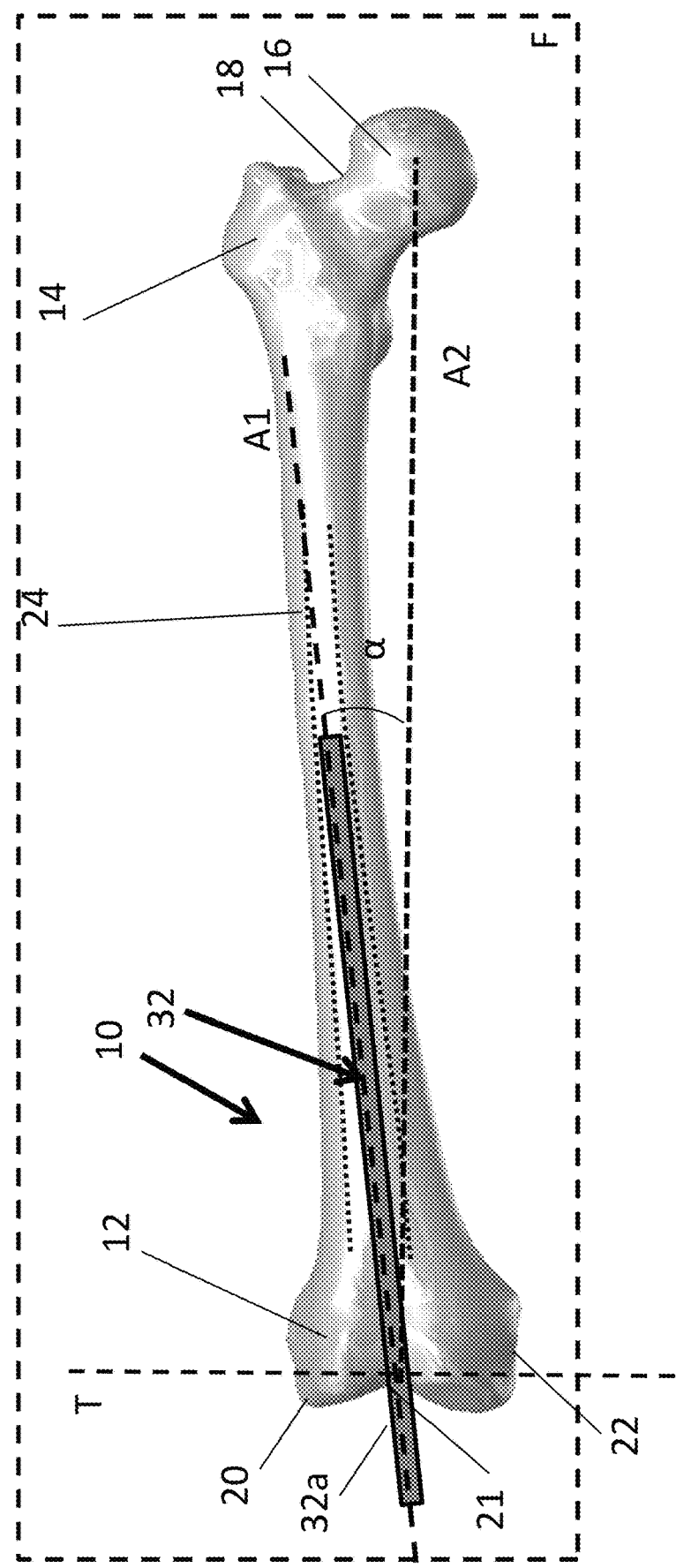
FIG. 4 is a schematic view of a fixing rod of the patient-specific cutting block of FIG. 3 inserted in the intramedullary canal of the femur of FIG. 1.

The structure 36 includes a bore 40 (shown in FIG. 3) which is designed to position the structure 36 in a predetermined orientation to, in turn, position the cutting guide 37 along a desired cutting plane. The positioning of the bore 40 in the structure 36 may therefore be patient specific, such that the assembly of the structure 36 onto the fixing rod 32 via the bore 40 results in a planned unique coupling orientation of the structure 36 relative to the bone. When the patient-specific cutting assembly 30 is assembled onto the femur 10, the bore 40 receives the fixing rod 32. As such, the bore 40 is dimensioned to have a diameter larger than that of the fixing rod 32, for sliding movement thereon. In one embodiment, the diameter of the bore 40 is slightly larger than that of the fixing rod 32 to reduce any play therebetween. In addition, to provide the desired orientation of the structure 36, the bore 40 is disposed at a predetermined orientation relative to the opposed faces 38, 39 as mentioned above. It is also contemplated to provide a unique coupling orientation joint between the portion 32a of the fixing rod 32 and the bore 40, to reach the unique coupling orientation of the structure 36 relative to the bone. In the embodiment shown in the figures, the predetermined orientation corresponds to an angle α between the bore 40 and the opposed faces 38, 39. The angle α shown in the figures is an absolute angle. It may be decomposable into two angles projected respectively on the frontal plane F and a sagittal plane S (shown in FIG. 1). The angle α is chosen based on an orientation of the fixing rod 32 relative to the femur 10 when the fixing rod 32 is inserted in the intramedullary canal 24, i.e. axis A1, and on an orientation of a predetermined bone axis A2, for instance combining the angles along the transverse plane T and the frontal plane F. The axes A1 and A2 are shown in FIG. 4.

The axis A1 may be defined as the axis of the fixing rod 32 when the fixing rod 32 is inserted in the intramedullary canal 24. The orientation of the axis A1 may thus be determined preoperatively, after modelling the insertion of the fixing rod 32 into the intramedullary canal 24 using data of the femur 10 from, for example, pre-operative radiographic images, to determine an orientation of the intramedullary canal 24 and data of the selected fixing rod 32. In another example, the axis A1 may be defined as an axis passing at equidistance between walls of the intramedullary canal 24.

The axis A2 may be defined as an axis based on loads experienced by the femur 10 during normal use and/or connections to the other bones (pelvis and knee). For example, the axis A2 may be defined as the mechanical axis passing through the center of the femoral head 16 and the midpoint 21 (shown in FIG. 4) between the condyles 20, 22. Other definitions of the axis A2 are contemplated, as desired by the user of the system. The determination of the axis A2 may be using data of the bone, such as the X-rays or a 3-D model of the bone. Virtual modelling of the bone 10 and the loads may also be used to determine the axes A1 and A2.

The axes A1 and A2 are determined in a non-invasive pre-operative manner and before manufacturing the structure 36 so that the bore 40 may be formed in the structure 36 at the angle α desired such that once the fixing rod 32 and structure 36 are in place on the femur 10, the structure 36 provides the desired orientation for the cutting guide 37, simply by positioning the structure 36 on the fixing rod 32, without the subsequent need for intraoperative navigation to adjust the orientation of the structure 36.

Figure 5:
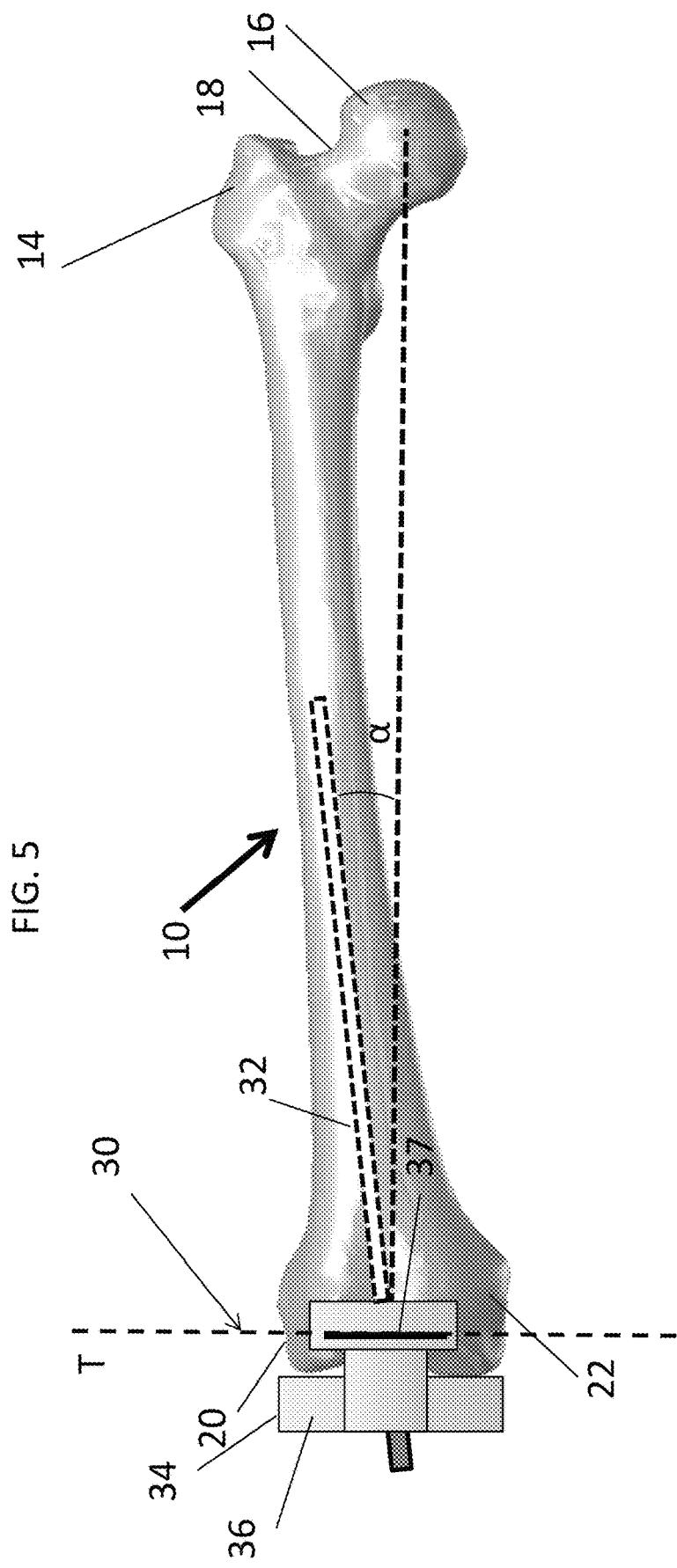
FIG. 5 is a schematic view of the femur of FIG. 1 shown with the patient-specific cutting block of FIG. 3 assembled to the fixing rod.
Figure 6:
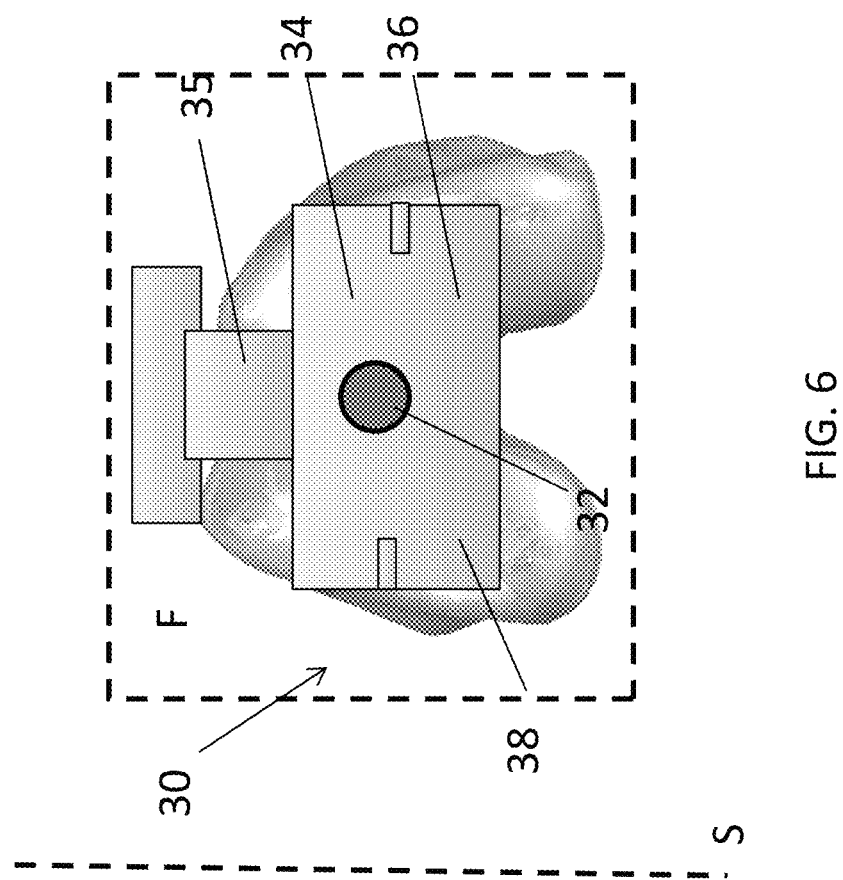
FIG. 6 is a schematic view of FIG. 5 shown from a different angle.

In a femoral knee embodiment, the structure 36 may accommodate the attachment 35 in three distinct positions, so that the cutting guide 37 may be positioned to cut the femur 10 along the three different planes: transverse, frontal anterior and frontal posterior. The structure 36 could accommodate more or less than three distinct cutting positions, for examples by providing drill positions, and defines planes other than transverse and frontal. The planes corresponds to planes defined in the implant and through which the implant and the femur 10 will connect in coplanar fashion, and may include oblique planes. In the embodiment shown in the figures, the cutting guide 37 is disposed so as to perform cuts parallel to a transverse plane T. As shown in FIG. 5, the transverse plane T is parallel to the faces 38, 39 of the structure 36. The cutting guide 37 is disposed at a distance d (shown in FIG. 3) from the face 39 which is determined based on the implant selected (i.e. depth of the inside of the implant). The cutting guide 37 could be disposed along another plane after the cut along the transverse plane T. The other plane may be a plane perpendicular to the transverse plane T or at an angle with the transverse plane T. As such, the cutting guide 37 can be used to sequentially cut along different predetermined planes.

Figure 7:
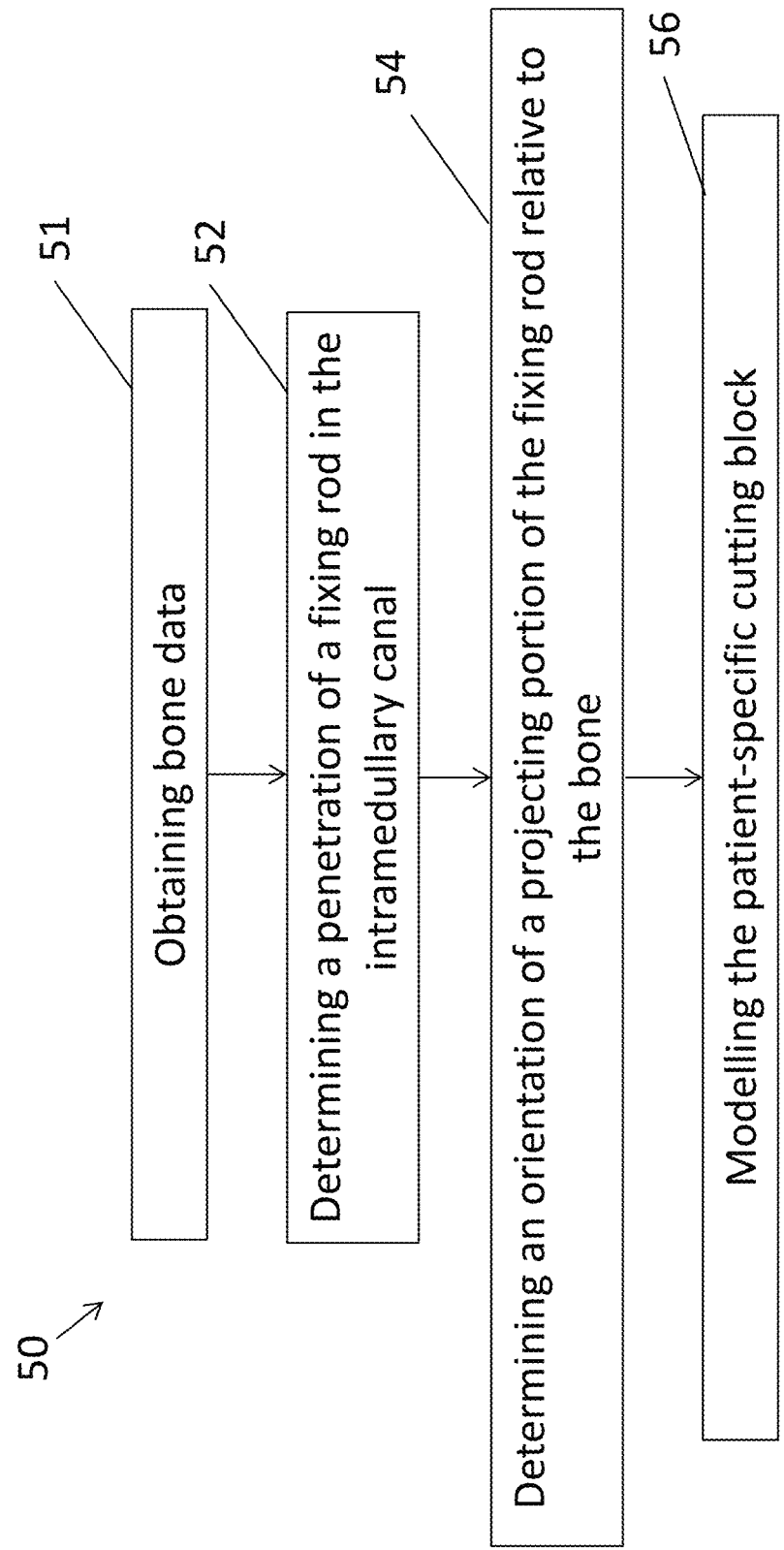
FIG. 7 is a flow chart of a method of manufacturing the patient-specific cutting block of FIG. 3.

Turning now to FIG. 7, a method 50 of manufacturing the patient-specific cutting block 30 will be described. The method 50 is performed before surgery in order to provide a patient-specific bone cutting assembly or a patient-specific portion thereof.

According to 51, bone data is obtained, using imaging of the bone. For example, a model of the bone may be created. The bone data may include size, diameter and/or geometry of the intramedullary canal 24, and a model of the bone surface to be resurfaced, as well as axes, such as a mechanical axis of the femur F in the case of knee joint surgery.

The method 50 has a step 52 of determining the orientation of the fixing rod 32 as inserted in the intramedullary canal 24. The geometry of the intramedullary canal 24 may be determined from the bone data obtained at 51. Based on the dimension and shape of the intramedullary canal 24, a fixing rod 32 may be selected as described above. Alternatively, a fixing rod 32 specific to the patient may be designed in accordance with the geometry of the intramedullary canal 24 of the patient, ensure a specific and unique-orientation fit of the fixing rod 32 in the intramedullary canal 24. Modelling can be used to virtually insert the selected fixing rod 32 into the intramedullary canal 24 in order to determine an orientation of the portion 32a of the fixing rod 32 relative to the surrounding bone, for instance by determining axis A1. Other techniques can be used to determine the orientation of the portion 32a relative to femur F.

From step 52, the method 50 goes to step 54 where the orientation of the cut planes are determined. For example, the orientation of the cut planes may be based on the bone axis A2 (mechanical axis) based on an operator's preference in planning surgery, for instance in a fashion described above. For example, it may be desired that the bone axis A2 be normal to a transverse cut plane. Likewise, the anterior frontal and posterior frontal planes may be parallel to the bone axis A2, and perpendicular to the transverse cut plane. The bone axis A2 may have been drawn onto radiographic images or been virtually modelled onto a 3-D model of the femur 10 in step 51. Other ways to determine the orientation of the cut planes and/or indicate the bone axis A2 are contemplated. Then, the orientation of the bone axis A2 and of the fixing rod 32 inside the intramedullary canal 24 may be used to determine an orientation between them, for example using the angle α described above.

From step 54, the method 50 goes to step 56, where the patient-specific cutting block 30 is modeled based on the orientations of the axis A1 and A2 and on the orientation of the cut planes. As such, the method 50 may take into consideration the size of the implant that will be used. A portion (such as the structure 36) of the cutting block 30 or the entirety of the cutting block 30 can be modeled to be patient-specific. In the example below, the structure 36 is modeled to be patient specific. The model includes the bore 40 formed in the structure 36 at an angle related to the angle α, which indicates the orientation between the axes A1 and A2 and is thus patient specific as it was determined based on preoperative planning specific to the client. In one embodiment, the angle α corresponds to the orientation between the axis A1 and the axis A2 in the transverse plane and the frontal plane. However, modelling at step 54 may include only knowing relative orientations of the parts so as to select the structure 36 and form the bore 40 in accordance to the axis A1 and A2, and not necessarily 3-D modelling of the structure 36.

The method 50 may be followed by the steps of creating instructions based on the model of the structure 36 for manufacturing the structure 36, and manufacturing the structure 36 based on the instructions. The method 50 may also include selecting from a pool of attachments 35 or manufacturing the attachments 35 based on patient's data such that the cutting guide 37 is at the distance d according to the implant selected, the distance d being determined by the dimensions of the implant. Similarly, the cutting guide 37 may be selected form a pool of cutting guides 37 or manufactured based on patient's data and on the distance d. The implant may be selected based on patient data, and the implant characteristics may be provided so that the distance d may be determined.

Once the structure 36 is manufactured, the assembly of the structure 36, attachment 35 and cutting guide 32, if required, is performed intraoperatively.

Turning now to FIG. 8, a method 60 of cutting the femur 10 with the patient-specific cutting block 30 in preparation of placement of the implant thereonto will be described.

At step 62, with the femur resected or machined to expose the intramedullary canal, the fixing rod 32 is inserted longitudinally in the intramedullary canal 24 of the femur 10 such that the portion 32a of the fixing rod 32 extends outside the bone in the predicted manner.

At step 64, once the fixing rod 32 is inserted, the structure 36 may be installed onto the portion 32a, for instance until abutment with the lower end 12 of the femur 10. The structure 36, once inserted onto the fixing rod 32, may be rotated around the fixing rod 32 until being blocked in a desired position. For this purpose, the structure 36 may have abutments positioned to ensure that the structure 36 has a unique coupling orientation of abutment against the bone when installed onto the portion 32a. In one embodiment, the structure 36 is rotated so as to abut the posterior condyles. Other ways to position the structure 36 relative to the bone 10 are contemplated, such as complementary mating or abutment. The bore 40 provides a fixed patient-specific orientation of the structure 36 relative to the bone 10. As such, when the structure 36 is inserted, there may be no adjustment of the orientation of the structure 36 relative to the femur 10, as the structure 36 may necessarily adopt the unique coupling orientation. It may be necessary to rotate the structure 36 about the portion 32a to ensure that a desired orientation is reached. For this purpose, the structure 36 may have a visual marker to be aligned with the midpoint 21 (FIG. 4), or may have a projecting abutment that will abut against the bone in the predicted orientation, as alternatives to the patient specific second face 39. For instance, the attachment 35 may be positioned onto the structure 36 and the cutting guide 37 placed in abutment with the bone, to serve as the means for aligning the structure 36 in a degree of freedom of orientation that is about the axis of the fixing rod 32, if the portion 32a is round in cross-section. Other examples to set the rotation include one or more visual markers aligned with bony landmarks (e.g. epicondylar axis), surfaces on the patient-specific cutting block 30 matching a shape of the bone 10, abutment against the bone or cartilage, and abutment against posterior condyles.

In step 66, the bone may be cut along the transverse plane T (or another plane, depending on the cutting guide 37 position, as discussed above). The attachment 35 positions the cutting guide 37 at the distance d predetermined in function of the implant. It may be required that the structure 36 be pinned down to the bone, and the fixing rod 32 be removed, prior to cutting the bone.

The above device and methods allow to adapt the cutting tools to each patient so as to provide more precise cutting and therefore better fit of the implant. The above methods may be performed with already existing images of the bones or with new images of the bone. The patient-specific cutting block may be manufactured using a pool of structures, rods and cutting attachments and customising the bore orientation and the distance between the cutting guide and the structure.

The above description is meant to be exemplary only, and one skilled in the art will recognize that changes may be made to the embodiments described without departing from the scope of the invention disclosed. Other modifications which fall within the scope of the present invention will be apparent to those skilled in the art, in light of a review of this disclosure, and such modifications are intended to fall within the appended claims.

The invention claimed is:

1. A patient-specific cutting assembly, the assembly comprising:
   a model file including geometrical data of a bone of the patient, of an intramedullary canal of the bone, and a planned orientation of a cutting block;
   a fixing rod adapted to be longitudinally inserted in and extending partially from the intramedullary canal; and
   a patient-specific cutting block connectable to the fixing rod, the patient-specific cutting block including at least:
      a structure having a patient specific geometry corresponding to the model file of the patient, the structure configured to be connected to a portion of the fixing rod projecting from the bone to reach a unique coupling orientation with the structure coupled to the bone when the structure is connected to a portion of the fixing rod; and
      a cutting guide connected to the structure, the cutting guide being in the planned orientation when the structure is connected to the portion of the fixing rod projecting from the bone.

2. The patient-specific cutting assembly according to claim 1, wherein the structure has a bore extending through opposed first and second faces thereof, the bore having a diameter allowing the fixing rod to be inserted thereinto, the bore being formed in the structure at an orientation based on the model file.

3. The cutting assembly as defined in claim 2, wherein an orientation of the bore in the structure is based on a predetermined bone axis.

4. The cutting assembly as defined in claim 3, wherein the predetermined bone axis is a mechanical axis of the bone.

5. The cutting assembly as defined in claim 1, wherein a face of the structure is adapted to abut the bone, the face of the structure has a shaped that is a negative of a surface of the bone obtained as the geometrical data of the bone of the patient.

6. The cutting assembly as defined in claim 1, wherein the fixing rod has a geometry that is a negative of an inner surface of the intramedullary canal obtained as the geometrical data of the intramedullary canal.

7. A method of cutting a bone of a patient in preparation of placement of an implant onto the bone, the method comprising, sequentially:
   inserting a fixing rod longitudinally in an intramedullary canal of the bone with a portion of the fixing rod extending outside the bone;
   connecting a patient-specific structure of a cutting block onto the portion of the fixing rod extending outside the bone and placing a cutting guide of the patient-specific cutting block in abutment with the bone, while the structure is coupled to the bone in a unique coupling orientation; and
   cutting the bone with the cutting guide.

8. The method as defined in claim 7, wherein connecting the patient-specific structure comprises anchoring the patient-specific structure to the bone and removing the fixing rod.

\* \* \* \* \*